United States Patent [19]

Stavropoulos et al.

[11] 4,142,938
[45] * Mar. 6, 1979

[54] DETERMINATION OF TRIGLYCERIDES AND GLYCEROL

[75] Inventors: William S. Stavropoulos, Carmel; Robert D. Crouch, Indianapolis, both of Ind.

[73] Assignee: The Dow Chemical Company, Midland, Mich.

[*] Notice: The portion of the term of this patent subsequent to Jan. 4, 1994, has been disclaimed.

[21] Appl. No.: 730,920

[22] Filed: Oct. 8, 1976

Related U.S. Application Data

[63] Continuation of Ser. No. 452,879, Mar. 20, 1974, Pat. No. 4,001,089.

[51] Int. Cl.² .................... C07G 7/02; G01N 31/14
[52] U.S. Cl. ............................... 195/63; 195/99; 195/103.5 R
[58] Field of Search .................. 195/103.5 R, 99, 63

[56] References Cited

U.S. PATENT DOCUMENTS

| | | | |
|---|---|---|---|
| 3,703,591 | 11/1972 | Bucolo et al. | 195/103.5 R |
| 3,713,986 | 1/1973 | Bergmeyer et al. | 195/103.5 R |
| 4,056,442 | 11/1977 | Huang et al. | 195/99 |

OTHER PUBLICATIONS

Klotzsch et al., Abstract CC31, Technicon International Congress, Technicon Instruments Corporation (1972).

Wieland, "Method of Enzymatic Analysis", by Bergmeyer, Academic Press, N. Y. & London, (1965) pp. 211–214.

Hycel Brochure on Triglyceride Test by Hycel, Inc., 1975.

*Primary Examiner*—David M. Naff

[57] ABSTRACT

Triglycerides in biological fluids containing interfering substances, such as phospholipids, are determined by hydrolyzing the triglycerides to glycerol in a short time span at moderate temperatures with a solution of alkali metal hydroxide in methanol, and treating the resultant hydrolysis mixture with a water soluble magnesium salt to precipitate the interfering substances. Glycerol is then colorimetrically determined in the resultant supernatant solution by incubating with a single reagent-substrate composition to develop a measurable color.

9 Claims, No Drawings

DETERMINATION OF TRIGLYCERIDES AND GLYCEROL

This is a continuation of application Ser. No. 452,879, filed Mar. 20, 1974, now U.S. Pat. No. 4,001,089.

BACKGROUND OF THE INVENTION

Colorimetric determinations of glycerol and of mono-, di-, and triglycerides (usually reported simply as "triglycerides") in biological fluids are carried out by various methods in many laboratories. The value of such determinations as an aid in diagnosis of atherosclerosis, diabetes mellitus, nephrosis and various other conditions is well established. See, Henry, Clinical Chemistry, Hoeber Division, Harper & Row, New York (1964), 864–870. The methods typically involve separation of triglycerides (as well as mono- and diglycerides) from other lipids such as phospholipids by extraction or chromatography. The separated triglycerides are then hydrolyzed to produce glycerol, which is then analyzed chemically, by chemical oxidation to formaldehyde and assay of the formaldehyde or by enzymatic determination. The enzymatic procedure uses the enzymes glycerol kinase ("GK", also referred to as "glycerokinase") glycerol-1-phosphate dehydrogenase (G-1-PDH) in the presence of adenosine-5-triphosphate (ATP) and oxidized nicotinamide adenine dinucleotide (NAD), according to the following scheme:

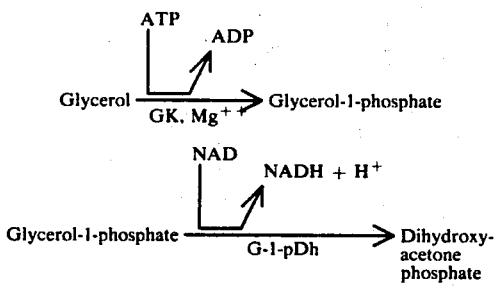

The reduction of NAD to NADH can be followed by ultraviolet spectroscopy. The glycerol determination can also be carried out by ultraviolet assay using glycerol dehydrogenase to catalyze the reaction:

Glycerol + NAD → NADH + dihydroxyacetone

In the GK, G-1-PDH catalyzed procedure, hydrazine has usually been added to the reaction mixture to react with the dihydroxyacetone phosphate, to drive the reaction to the right. See, for example, Spinella et al., J. Lipid Research, 7, pp 167–169 (1966).

Methods have been described in which serum samples are hydrolyzed with alcoholic base and the neutralized extracts are assayed colorimetrically by coupling the GK, G-1-PDH, reactions to the diaphorase-catalyzed reaction of NADH with the tetrazolium dye, INT. Klotzsch et al., Abstract CC31, Technicon International Congress "Advances in Automated Analysis", Technicon Instruments Corporation, Tarrytown, N.Y. (1972). However, the previous alcoholic base hydrolysis procedures required saponification in heated ethanolic potassium hydroxide for long periods at elevated temperatures (e.g., thirty minutes at 55°–70° C.). See, Carlson et al., Clin. Chim. Acta, 4, 197–205 (1959). Such methods have thus been regarded as undesirably time-consuming and laborious. See, Stork et al., U.S. Pat. No. 3,759,793.

BRIEF SUMMARY OF THE INVENTION

This invention is directed to an improved method for determination of triglycerides in biological fluids, and more particularly to an improved method of determining triglycerides in biological fluids, such as blood serum, which also contain interfering substances, such as phospholipids. In the method of the invention, the triglycerides in a biological fluid to be analyzed are hydrolyzed to glycerol in a short time span at moderate temperatures by a solution of an alkali metal hydroxide in methanol. The hydrolysis mixture is then treated with a water-soluble magnesium salt, to remove potential interfering substances such as phospholipids and the resulting precipitate is removed, for example, by centrifugation. The glycerol remaining in the resulting supernatant solution is then quantitatively determined to give a quantitative measurement of triglycerides. As in accepted procedures, glycerol, mono- and diglycerides are included in the triglycerides determination, and the results can be reported in terms of triglycerides.

The invention thus eliminates the need for time-consuming and difficult extractions, chromatographic separation, or high temperature saponification of triglycerides, and avoids the use of expensive lipases in hydrolysis. Additionally, it minimizes the risk of errors resulting from the solvent extraction and chromatography steps. The invention provides for determination of glycerol in a series of steps involving relatively simple liquid handling operations, and is thus readily adapted to automation. Further, in a preferred embodiment thereof the invention provides a rapid colorimetric determination of glycerol, thus permitting the simple, rapid determination of triglycerides with relatively inexpensive and uncomplicated equipment.

In carrying out the method of the invention, a biological fluid, such as human blood serum, is mixed with a solution of an alkali metal hydroxide in methanol. (Such a solution can also be referred to as a solution of an alkalimetal methoxide in methanol.) Alkali metal hydroxides such as lithium, sodium or potassium hydroxide can be used. Sodium hydroxide in methanol is preferred.

The concentration of the alkali metal hydroxide in the hydrolysis mixture and the relative proportions of the biological fluid sample and methanol solution are important to the successful practice of the invention. The alkali metal hydroxide, methanol and biological fluid specimen should be combined in proportions which provide a final hydrolysis mixture containing from about 75 to about 99.9 percent by weight of methanol, or from about 5 to about 1000 parts by volume (milliliters) of methanol per part by volume (milliliters) of specimen, and in which the alkali metal hydroxide concentration is from about 0.15 to about 0.5 Normal. In general, good results can be obtained in biological fluids such as human blood serum by mixing from about 0.020 to about 0.2 milliliters of biological fluid specimen with about one milliliter of methanol solution of alkali metal hydroxide which is from about 0.2 Normal to about 0.4 Normal, (corresponding to a hydrolysis mixture containing from about 79.8 to about 97.5 percent by weight of methanol). The use of insufficient methanol or base tends to give low results; and substantially higher concentrations of base can give undesirably elevated results. The biological fluid is preferably mixed with a methanol solution of the hydroxide which is from about 0.27 to about 0.37 Normal, and from about 5 to about 50 parts by volume of the methanol solution are employed per part by volume of biological fluid specimen (volume in milliliters).

The resulting mixture is then held for a brief period of time sufficient for substantially complete hydrolysis of triglycerides to take place. In general, the holding time can be from about 1 to about 5 to about 10 to about 15 to about 20 minutes at a temperature of about 25° to about 40° C., the optimum time decreasing at temperature increases. Good results are obtained with ten minutes hydrolysis time at 37° C., with a mixture which is 0.32 Normal in sodium hydroxide and in which the volumetric ratio (in milliliters) of specimen to methanol is one to ten.

After the hydrolysis period, the mixture is mixed with an aqueous magnesium salt solution according to known procedures to precipitate interfering substances such as phospholipids and the resulting precipitate is removed. Precipitation with magnesium sulfate or magnesium chloride followed by centrifugation or filtration is a simple and inexpensive operation. It is preferred to add aqueous 0.05 to 0.3 molar magnesium sulfate or magnesium chloride, and then centrifuge to remove the resulting precipitate. The glycerol can then be determined in the resulting supernatant liquid.

The glycerol determination can be carried out by classical procedures. However, it is preferably carried out by an improved procedure which is particularly well suited to determination in a biological fluid hydrolysate produced as described above. In the improved procedure, glycerol is determined by enzymatically converting the glycerol to glycercol-1-phosphate with ATP and $Mg^{++}$; enzymatically converting the glycerol-1-phosphate to dihydroxyacetone phosphate with oxidized nicotinamide adenine dinucleotide (NAD), thereby reducing the NAD to reduced form, NADH; and determining the amount of NADH formed. Preferably the NADH is determined by reacting it in the presence of an electron carrier with a colorless tetrazolium dye adapted to form a colored product in such reaction, and photometrically determining the amount of resulting colored tetrazolium product. The photometric determination can be carried out using a colorimeter or photometer capable of measuring absorbance or transmittance of light in the visible spectrum.

All the materials necessary for the improved glycerol determination can be formulated in a single reagent-substrate composition, and the reactions can thus be carried out substantially simultaneously. In a convenient procedure, the hydrolyzed biological fluid specimen (now containing free glycerol from the hydrolysis) is incubated with a reagent-substrate composition comprising adenosine triphosphate (ATP), oxidized nicotinamide-adenine dinucleotide (NAD), a source of magnesium ion (e.g., water soluble magnesium salt), glycero kinase (GK), glycerol-1-phosphate dehydrogenase (G-1-PDH), an electron carrier such as diaphorase or N-methyl phenazonium methosulfate (PMS); a colorless tetrazolium dye, such as 2-p-iodophenyl-3-nitrophenyl-5-phenyltetrazolium chloride (INT), which is capable of forming a colored product in an electron carrier-catalyzed reaction with reduced nicotin-amide adenine dinucleotide (NADH) and which does not react detrimentally with the other ingredients or with other materials present during the incubation. The resulting mixture is incubated under conditions conducive to the foregoing reactions for a time sufficient to produce a colorimetrically measureable amount of the colored tetrazolium product, and the amount of the product is measured. Triglycerides content of the specimen can be determined from the result by comparison to results obtained with standard solutions of known triglycerides content, comparison to standard curves, etc.

The reagent-substrate composition preferably contains the following ingredients in the following proportions:

For the phosphorylation of glycerol to glycerol-1-phosphate:
  ATP — from about 5 to about 30 grams or more
  Glycerol Kinase — from about 1000 to about 10,000 or more International Units (I.U., determined by assay at 30° C.)
  Magnesium Source, e.g., $MgCl_2.6H_2O$ — from about 0.0009 to about 0.074 moles or more For conversion of glycerol-1-phosphate to dihydroxyacetone phosphate, and NAD to NADH:
  G-1-PDH — from about 5000 to about 280,000 I.U. (determined by assay at 25° C.)
  NAD — from about 20 to about 120 grams or more For the tetrazolium dye color reaction:
  Tetrazolium dye (INT) — from about 0.5 to about 5 grams or more
  Diaphorase — from about 1600 to about 8050, to about 10,000 I.U. or more (I.U.s determined by assay at 25° C.)

The foregoing ingredients are preferably dispersed in an aqueous buffer at a suitable pH (e.g., about 6.8 to about 8.9, preferably, 7.5 to 8.75) in proportions corresponding to the foregoing amounts in about 15 liters of buffer. The maximum concentrations of ATP, GK, magnesium source, NAD, INT, and diaphorase do not appear to be critical, and such ingredients, particularly the GK and diaphorase, can be employed in amounts from the minimums stated above to saturation of the ultimate mixture with the specimen. However, good results are obtained within the above numerical proportion ranges.

Ammonium sulfate, normally present in some enzyme preparations, and hydrazine are not necessary in the composition, and the composition is preferably essentially free of ammonium sulfate and hydrazine, e.g., it has ammonium sulfate and hydrazine concentrations below that sufficient to exert a significant measurable effect on the enzyme catalyzed reactions and preferably no detectable hydrazine. When ammonium sulfate enzyme preparations are to be used, they are preferably dialyzed by conventional procedures to remove ammonium sulfate before being incorporated in the reagent substrate composition. Additional ingredients can be added, such as stabilizers, surfactants, or lyophilization stabilizers such as albumin.

From about one to about ten or more milliliters of the reagent substrate composition (preferably from about two to about five milliliters) are used per milliliter of the hydrolysis mixture obtained by treatment of the biological fluid with methanolic base. The resulting mixture is incubated at a temperature of from about 25° to 30° to 45° C., preferably about 37° C., until a measurable color develops. The incubation period is usually from about one minute or less to about 10 minutes to about 20 minutes. The time required for equivalent color development increases as temperature decreases; and the incubation is preferably carried out at from about 35° to about 40° C. for from about one to about 3 to about 12 minutes. In most cases, color development is substantially complete in about 3 minutes at 37° C. The reactions can be terminated after a predetermined time period by adding an excess of an acid such as hydrochloric acid. The color, which is stable for about 15 minutes after addition of acid, can be measured in a colorimeter or spectrophotometer with light having a wavelength of about 475 to about 530 nanometers. Alternatively, the color can be measured after a predetermined incubation period without terminating the incubation, as may be more convenient when automatic analysis equipment is employed. In such cases the color can generally be measured after very short incubation times, e.g. one to three minutes at 37° C., since precise timing can provide good results with color development which is less than complete.

The reagent-substrate composition can be prepared as a concentrate and lyophilized, if desired. The resulting lyophilized composition is adapted for storage and handling at ambient or refrigerated temperatures, and is reconstituted with buffer before use.

The following examples illustrate the invention:

EXAMPLE 1

A reagent-substrate composition is prepared by mixing the following ingredients in the following proportions:

| | |
|---|---|
| Magnesium Chloride (Hexahydrate) | 6 grams |
| ATP | 18 grams |
| NAD | 72 grams |
| Bovine Albumin (Stabilizer) | 16 grams |
| Glycerol kinase solution (1400 International Units per milliliter) | 6 ml. |
| Glycerol-1-phosphate dehydrogenase (2000 I.U. per milliliter) | 60 ml. |
| Diaphorase | 7705 I.U. |
| Aqueous 0.10 molar, 2-amino--2-methyl-1,3-propanediol-HCl buffer, pH 8.1 at 37° C. q.s. to 15 liters | |

The reagent-substrate composition is dispensed into colorimeter vials, 1.5 ml. per vial.

The composition is used in triglyceride assays as follows:

0.1 Milliliter of human serum specimen, 0.1 ml. of a triolein standard solution (200 mg triolein per 100 ml.) and 0.1 ml. of distilled water are transferred to vials designated "sample", "standard" and "blank", respectively. 1.0 Milliliter of 0.32 Normal sodium hydroxide in methanol is added to each vial. The resulting hydrolysis mixtures are mixed well and held for 10 minutes in a 37° C. heating block. 1.0 Milliliter of aqueous 0.15 molar magnesium sulfate solution is mixed with the contents of each vial and the vials are centrifuged at 1150 gravities — (1150 X g) for five minutes to separate the resulting precipitate.

0.5 Milliliter of the resulting clear supernatant from each vial is added to the 1.5 ml. of substrate-reagent composition in each of three correspondingly labeled (sample, standard, blank) vials. The vials are incubated for 5 minutes at 37° C., after which the incubation is terminated by addition of 0.5 ml. of 0.1 Normal hydrochloric acid to each vial.

The color in each vial is measured by measuring absorbance in a colorimeter with light having a wavelength of 500 nanometers. The triglycerides content of the sample is then calculated by dividing the absorbance difference between the sample and the blank vials by the absorbance difference between standard and the blank vials, and multiplying the quotient by the known triglyceride-concentration of the triolein standard solution (200 mg per 100 ml).

In other operations, good results are obtained using one ml. of 0.1 Normal hydrochloric acid to terminate the incubation after 5 minutes.

EXAMPLE 2

The compositions and first described method of Example 1 are employed to determine triglycerides content of human serum in 105 serum samples having triglycerides concentrations ranging from about 50 to about 510 milligrams per 100 milliliters. A separate series of samples of identical sera is assayed by the method of Kessler and Lederer, "Automation in Analytical Chemistry", pp. 341–344, Skeggs, Ed., Mediad, N.Y. (1966). A statistical correlation study of the results indicates an excellent linear correlation between the methods, with a correlation coefficient of 0.9902 and standard deviation of 10.68.

EXAMPLE 3

The reagent and procedure are used to determine triglycerides concentration in five aliquots from the same serum pool. Five aliquot samples are analyzed daily for four consecutive days. The mean of the twenty determinations is found to be 386 milligrams per 100 milliliters, with a precision of ± 2.85 percent (95 percent confidence limits).

What is claimed is:

1. A reagent composition essentially free of hydrazine and useful for determining glycerol concentrations in biological fluids comprising from about 0.0009 to about 0.074 molar proportions of magnesium ion source; from about 5 to about 30 parts by weight (gram basis) of adenosine-5-triphosphate; from about 20 to about 125 parts by weight (gram basis) of oxidized nicotinamide adenine dinucleotide; from about 0.5 to about 5 parts by weight (gram basis) of a colorless tetrazolium dye adapted to form a colored reaction product in an electron-carrier catalyzed reaction with reduced nicotinamide adenine dinucleotide; from about 1000 to about 10,000 parts (International Unit basis) of glycerol kinase; from about 5000 to about 280,000 parts (International Unit basis) of glycerol-1-phosphate dehydrogenase; and from about 1600 to about 10,000 parts (International Unit basis) of diaphorase.

2. The composition of claim 1 further comprising about 15 parts by volume (liter basis) of aqueous buffer having a pH from about 6.8 to about 8.9.

3. Composition of claim 1 wherein the composition contains from about 10,000 to about 60,000 parts (International Unit basis) of glycerol-1-phosphate dehydrogenase.

4. A method useful for colorimetric determination of glycerol, comprising mixing a liquid specimen containing glycerol to be determined with a reagent substrate composition essentially free of hydrazine and comprising from about 0.0009 to about 0.074 molar proportions of magnesium ion source; from about 5 to about 30 parts by weight (gram basis) of adenosine-5-triphosphate; from about 20 to about 125 parts by weight (gram basis) of oxidized nicotinamide adenine dinucleotide; from about 0.5 to about 5 parts by weight (gram basis) of a colorless tetrazolium dye adapted to form a colored reaction product in an electron-carrier catalyzed reaction with reduced nicotinamide adenine dinucleotide;

from about 1000 to about 10,000 parts (International Unit basis) of glycerol kinase; from about 5000 to about 280,000 parts (International Unit basis) of glycerol-1-phosphate dehydrogenase; and from about 1600 to about 10,000 parts (International Unit basis) of diaphorase in about 15 parts by volume (liter basis) of aqueous buffer having a pH from about 6.8 to about 8.9 incubating the resulting mixture at a temperature from about 25° to about 45° C. and colorimetrically determining glycerol in the resulting mixture after from about 1 to about 20 minutes incubation.

5. Method of claim 4 wherein the reagent substrate composition contains from about 10,000 to about 60,000 parts (International Unit basis) of glycerol-1-phosphate dehydrogenase.

6. In a method for determining triglycerides in a biological fluid which comprises
    (a) hydrolyzing the triglycerides in the biological fluid to produce glycerol and fatty acids;
    (b) phosphorylating the resulting glycerol with adenosine triphosphate in the presence of glycerol kinase to produce glycerol-1-phosphate;
    (c) reacting the resulting glycerol-1-phosphate with oxidized nicotinamide adenine dinucleotide in the presence of glycerol-1-phosphate dehydrogenase, to produce reduced nicotinamide adenine dinucleotide; and
    (d) reacting the reduced nicotinamide adenine dinucleotide with a tetrazolium dye adapted to form a colored reaction product in the presence of diaphorase to produce a measurable color;
the improvement which comprises carrying out steps (b) (c) and (d) by;
    (e) mixing the glycerol produced in step (a) with a reagent composition which is essentially free of hydrazine and which comprises from about 0.0009 to about 0.074 molar proportions of a magnesium ion source; from about 5 to about 30 parts by weight (gram basis) of adenosine-5-triphosphate; from about 20 to about 125 parts by weight (gram basis) of oxidized nicotinamide adenine dinucleotide; from about 0.5 to about 5 parts by weight (gram basis) of a colorless tetrazolium dye adapted to form a colored reaction product in an electron-carrier catalyzed reaction with reduced nicotinamide adenine dinucleotide; from about 1000 to about 10,000 parts (International Unit basis) of glycerol kinase; from about 10,000 to about 60,000 parts (International Unit basis) of glycerol-1-phosphate dehydrogenase; and from about 1600 to about 10,000 parts (International Unit basis) of diaphorase;
    (f) incubating the resulting mixture for a time sufficient to develop a measurable color, whereby steps (b) (c) and (d) are carried out substantially simultaneously, and
    (g) measuring the resulting color after from about one to about 20 minutes incubation.

7. The method of claim 6 wherein the color measurement of step (g) is carried out after from about 3 to about 12 minutes incubation.

8. The method of claim 7 wherein the color is measured after about five minutes incubation.

9. The method of claim 6 wherein the incubation is carried out at a pH of from about 6.8 to about 8.9.

* * * * *